(12) United States Patent
Gonda

(10) Patent No.: US 9,301,727 B2
(45) Date of Patent: Apr. 5, 2016

(54) RADIOGRAPHIC IMAGING SYSTEM

(75) Inventor: Takaaki Gonda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 18 days.

(21) Appl. No.: 12/958,171

(22) Filed: Dec. 1, 2010

(65) Prior Publication Data

US 2011/0135063 A1 Jun. 9, 2011

(30) Foreign Application Priority Data

Dec. 3, 2009 (JP) .................................. 2009-275498

(51) Int. Cl.
*H05G 1/64* (2006.01)
*A61B 6/00* (2006.01)

(52) U.S. Cl.
CPC . *A61B 6/461* (2013.01); *A61B 6/56* (2013.01); *A61B 6/464* (2013.01)

(58) Field of Classification Search
CPC ........ A61B 6/461; A61B 6/462; A61B 6/464; A61B 6/56
USPC ................. 378/98.5, 98.8, 91, 98; 250/370.09
See application file for complete search history.

(56) References Cited

U.S. PATENT DOCUMENTS 5,068,883 A * 11/1991 DeHaan et al. .................. 378/86
2004/0114725 A1* 6/2004 Yamamoto ................... 378/98.8
2004/0188625 A1* 9/2004 Schulze-Ganzlin ......... 378/98.8
2006/0048196 A1* 3/2006 Yau ................................. 725/81
2006/0188071 A1* 8/2006 Spahn ........................... 378/196
2006/0202127 A1* 9/2006 Ozeki ....................... 250/370.01
2009/0046828 A1* 2/2009 Ohta et al. ........................ 378/1

FOREIGN PATENT DOCUMENTS

| JP | H06-102970 A | 4/1994 |
| JP | 2003-210444 A | 7/2003 |
| JP | 2004208749 A | 7/2004 |
| JP | 2005-006979 A | 1/2005 |
| JP | 2006150078 A | 6/2006 |
| JP | 2007-325500 A | 12/2007 |
| JP | 2008-518711 A | 6/2008 |
| JP | 2008134057 A | 6/2008 |
| JP | 2009048172 A | 3/2009 |
| JP | 2011-119123 A | 6/2011 |

OTHER PUBLICATIONS

Apple, "iPhone User Guide for iPhone OS 3.1 Software", (Sep. 9, 2009). Retrieved from the Internet: <URL: http://support.apple.com/manuals#iphone>.*

* cited by examiner

*Primary Examiner* — Glen Kao

(74) *Attorney, Agent, or Firm* — Canon USA Inc. IP Division

(57) ABSTRACT

A radiographic imaging system includes an imaging unit that detects radiation transmitted through a subject, an operation unit that controls the imaging unit, a signal sending and receiving device connects the imaging unit and the operation unit to each other by wired or wireless communication. A signal reception state display unit is disposed in the imaging unit or the signal sending and receiving device so as to display a signal reception state indicative of communication between the imaging unit and the signal sending and receiving device.

19 Claims, 7 Drawing Sheets

RADIOGRAPHIC IMAGING SYSTEM

BACKGROUND OF THE INVENTION

1. Field of the Invention

The present invention relates to a radiographic imaging system provided with a function for displaying a signal reception state between an imaging unit and a signal sending and receiving device.

2. Description of the Related Art

In recent years, a device that reproduces as a visible image based on a distribution of intensity of radiation transmitted through a subject by converting the radiation intensity distribution into electric signals and processing the electric signals has been widely used in an industrial nondestructive test and medical diagnosis. Also, along with recent progress of semiconductor processing technology, an apparatus for imaging a radiographic image in the same manner by using a semiconductor sensor has been developed.

As compared to conventional radiographic imaging systems using a photosensitive film, these systems have advantages of a considerably wide dynamic range and capability of obtaining a radiographic image that is less subject to a fluctuation in an amount of exposure to radiation. Further, since the systems do not require any chemical treatment as is different from the conventional system using a photosensitive film, the systems have the advantages of solving an issue of waste liquid treatment and instantaneously obtaining an output image.

The imaging apparatus of this type is generally installed and used in an imaging room, and there is a demand for an imaging apparatus that is thinner, of relatively low weight, and portable for the purposes of imaging during a round of a patient and imaging of various postures.

Also, since communication, electric power supply, and the like are enabled by connecting an imaging unit and an operation unit to each other through a cable, in the conventional imaging apparatus, the cable has been a cause of impairing operability when moving the imaging apparatus or performing imaging.

Accordingly, Japanese Patent Application Laid-Open No. 2003-210444 discusses an imaging apparatus and a wireless communication system for performing wireless communication between an imaging unit and an operation unit.

In general, in the case of wireless communication between an imaging unit and an operation unit, preparation for imaging is performed in an imaging room, and operation of the imaging unit and irradiation with radiation are performed in a control room. In the imaging method, a person who performs imaging (operator) goes back and forth between the two rooms of the imaging room and the control room. In some cases, an operator may not recognize that the wireless communication is impossible due to a bad signal reception state between the imaging unit and the operation unit until the operator sees a monitor installed in the control room. In such case, the operator has to go back to the imaging room again to perform the imaging preparation all over again.

Also, the wireless communication is in some cases used in X-ray imaging which is performed during a round of a patient. In the X-ray imaging during round visit, an imaging unit is inserted between a patient who is the subject and a bed or a wheelchair to perform imaging. In this case, an operator may not recognize that the wireless communication is impossible due to a bad signal reception state between the imaging unit and an operation unit until the operator sees a monitor on a portable X-ray generation device after performing the imaging preparation. In this case, too, the operator has to perform the imaging preparation all over again.

As described above, one of the issues in radiographic imaging by wireless communication is the problem of improper communication between components and the necessity therefore of the resetting work for the imaging preparation due to bad or inexistent signal reception.

SUMMARY OF THE INVENTION

The present invention is directed to a radiographic imaging system that solves the above-described problematic points and is capable of diminishing a resetting work for imaging preparation caused by a signal reception state.

A radiographic imaging system according to the present invention includes an imaging unit that is configured to detect radiation transmitted through a subject, an operation unit that is configured to control the imaging unit, and a signal sending and receiving device that is configured to connect the imaging unit and the operation unit to each other, wherein the imaging unit and the signal sending and receiving device include a sending and receiving unit that can be connected by wired communication or wireless communication, and the imaging unit or the signal sending and receiving device includes a signal reception state display unit that is configured to display a signal reception state between the imaging unit and the signal sending and receiving device.

Further features and aspects of the present invention will become apparent to persons having ordinary skill in the art from the following detailed description of exemplary embodiments with reference to the attached drawings, in which like reference characters designate the same or similar parts through the figures thereof.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
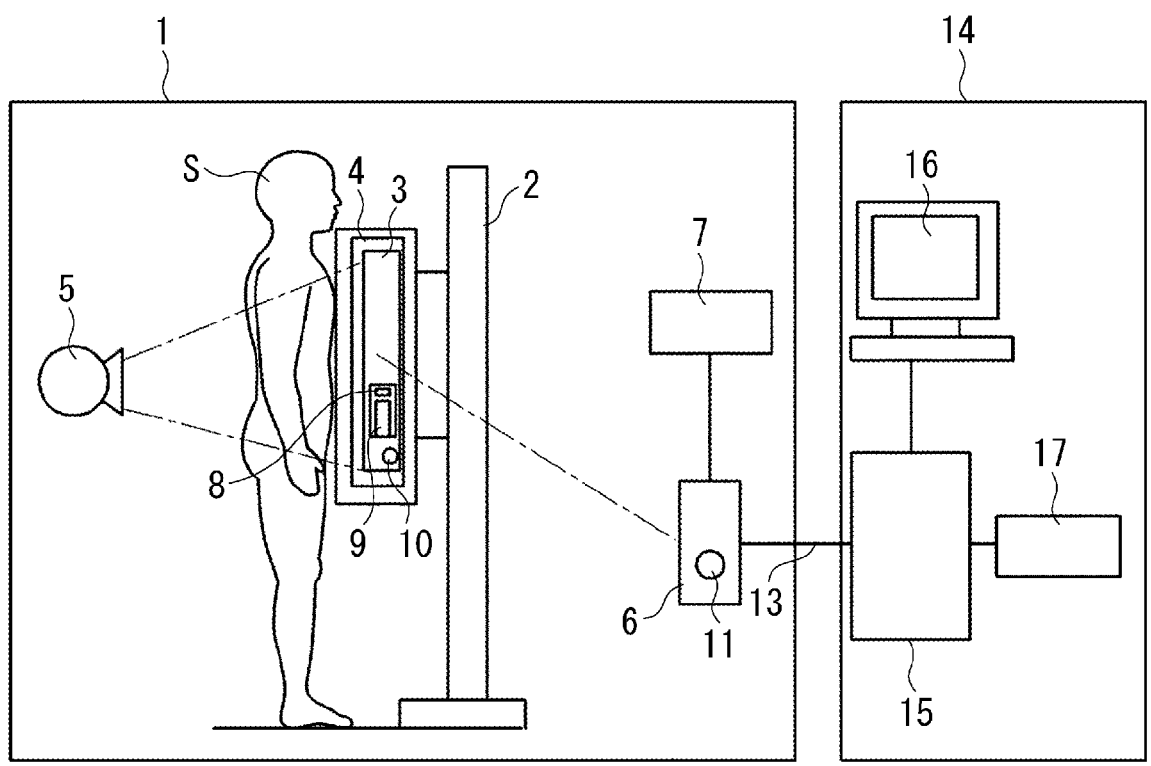
FIG. 1 is a diagram illustrating a radiographic imaging system according to a first exemplary embodiment.
Figure 2:
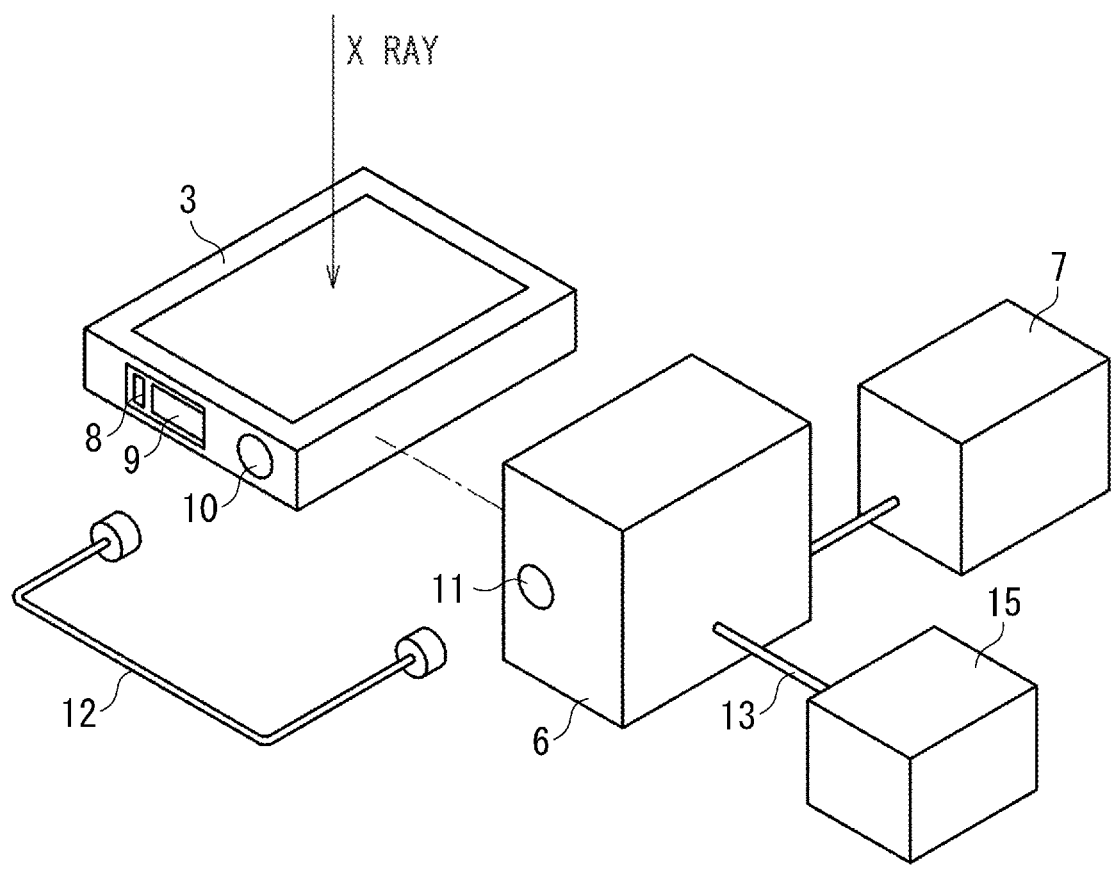
FIG. 2 is a diagram illustrating an imaging unit, a signal sending and receiving device, and an operation unit according to the first exemplary embodiment.

FIG. 1 is a diagram illustrating a radiographic imaging system intended for imaging in a hospital according to the first exemplary embodiment, and FIG. 2 is a diagram illustrating an imaging unit, a signal sending and receiving device, and an operation unit. In an imaging room 1, an upright mount 2 is disposed in front of a standing patient S who is the subject. A casing unit 4 housing an imaging unit 3 for acquiring an X-ray image is mounted on the upright mount 2. An X-ray tube 5 of an X-ray generation device for irradiating the patient S with an X-ray is provided at the rear of the patient S.

It is possible to incorporate a photo-timer for detecting radiation, a bucky unit for driving a grid for blocking a scattered radiation, and the like into an interior part of the casing unit 4. An X-ray detection sensor (not illustrated) that detects an intensity distribution of X-ray transmitted through the patient S and a battery (not shown) that supplies electric power to the imaging unit 3 are incorporated into the imaging unit 3.

The imaging unit 3 is connectable to a signal sending and receiving device 6 installed in the imaging room 1. More specifically, the imaging unit 3 is also equipped with a sending and receiving unit (not shown) that is connectable by way of wired communication or wireless communication to the signal sending and receiving device 6. An external power source 7 that is installed in the imaging room 1 is connected to the signal sending and receiving device 6.

A signal reception state display unit 8 to be used by a person who performs imaging (operator) for visual confirmation of a signal reception state between the imaging unit 3 and the signal sending and receiving device 6, and an imaging information display unit 9 formed of letters and images for confirmation of patient information and the like are provided side by side in the imaging unit 3. In the first exemplary embodiment, the signal reception state display unit 8 and the imaging information display unit 9 are preferably disposed at a lateral surface of the imaging unit 3. Any surface of the imaging unit 3 can be used except a radiation incident surface of the imaging unit 3. Specifically, it is preferable that the signal reception state display unit 8 and the imaging information display unit 9 be readily seen by the operator from any operating position in imaging room 1 without being concealed by the patient S or the like.

A cable connector 10 for the wired communication is provided on a lateral surface of the imaging unit 3. The cable connector 10 is connectable to a cable connector 11 provided in the signal sending and receiving device 6 via a cable 12 (shown in FIG. 2). The cable connector 10 provided on the imaging unit 3 may preferably be disposed on a surface except the radiation incident surface of the imaging unit 3 to prevent difficulty of connection from occurring due to the patient S or the like.

The signal sending and receiving device 6 is connected via a cable 13 to an operation unit 15 inside a control room 14 for performing control of X-ray imaging, image processing of an obtained X-ray image, and the like. Further, to the operation unit 15, a monitor 16 for displaying an imaged radiographic image, imaging conditions, patient information, and the like, and an input unit 17 such as a keyboard are connected. With such configuration, the imaging unit 3 and the signal sending and receiving device 6 are connected by wireless communication, and the signal sending and receiving device 6 and the operation unit 15 are connected via the cable 13.

During an imaging operation, the operator sets up an appropriate position relationship between the patient S and the upright mount 2 in the imaging room 1. Next, while staying within the premises of imaging room 1, the operator confirms a signal reception state by observing the signal reception state display unit 8 provided on the imaging unit 3, and confirms imaging conditions or patient information of the patient S by observing the imaging information display unit 9. Once the operator confirms that the signal reception state by the wireless communication between the imaging unit 3 and the signal sending and receiving device 6 is appropriate for X-ray imaging, the operator initiates imaging preparation.

However, when the signal reception state between the imaging unit 3 and the signal sending and receiving device 6 is inappropriate due to an influence of the upright mount 2 or the like, the cable connector 10 of the imaging unit 3 and the cable connector 11 of the signal sending and receiving device 6 are connected to each other by using the cable 12 to establish wired communication. After setting up the appropriate signal reception state by establishing the wired communication, the operator starts the imaging preparation.

Subsequently, the operator moves from the imaging room 1 to the control room 14 and irradiates the patient S with an X-ray from the X-ray tube 5 of the X-ray generation device by sending an imaging request signal from the operation unit 15. An X-ray image transmitted through the patient S is imaged as a digital image by a detection panel of the imaging unit 3, and the obtained image is transferred to the operation unit 15 to be displayed on the monitor 16.

As described above, since the operator can confirm the signal reception state and can select a communication method appropriate for the signal reception state in the imaging room 1 with the signal reception state display unit 8, it is possible to diminish a resetting work for the imaging preparation.

Also, an alarm for warning by a sound, vibration, or the like may be provided on the imaging unit 3 in addition to the signal reception state display unit 8, so that it is possible to give a warning to the operator by appealing to senses other than a visual sense if the signal reception state is not appropriate for the X-ray imaging.

Also, since the imaging unit 3 and the signal sending and receiving device 6 are connected via the cable 12 during the wired communication, it is possible to supply electric power for driving the signal sending and receiving device 6 and the imaging unit 3 from the external power source 7 when a battery level is low or critical in the imaging unit 3. Simultaneously, it is possible to charge the battery in the imaging unit 3 from the external power source 7. Moreover, cable 12 can be used to entirely replace the onboard battery of the imaging unit 3, for example, during replacement of such battery.

Figure 3A:
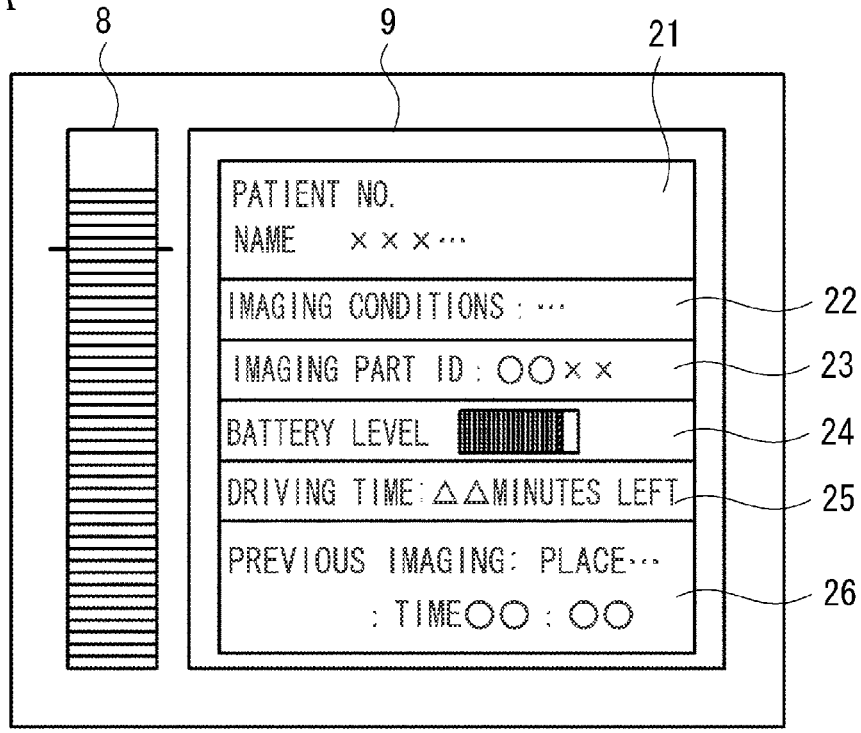
FIGS. 3A and 3B illustrate a signal reception state display unit and an imaging information display screen.
Figure 3B:
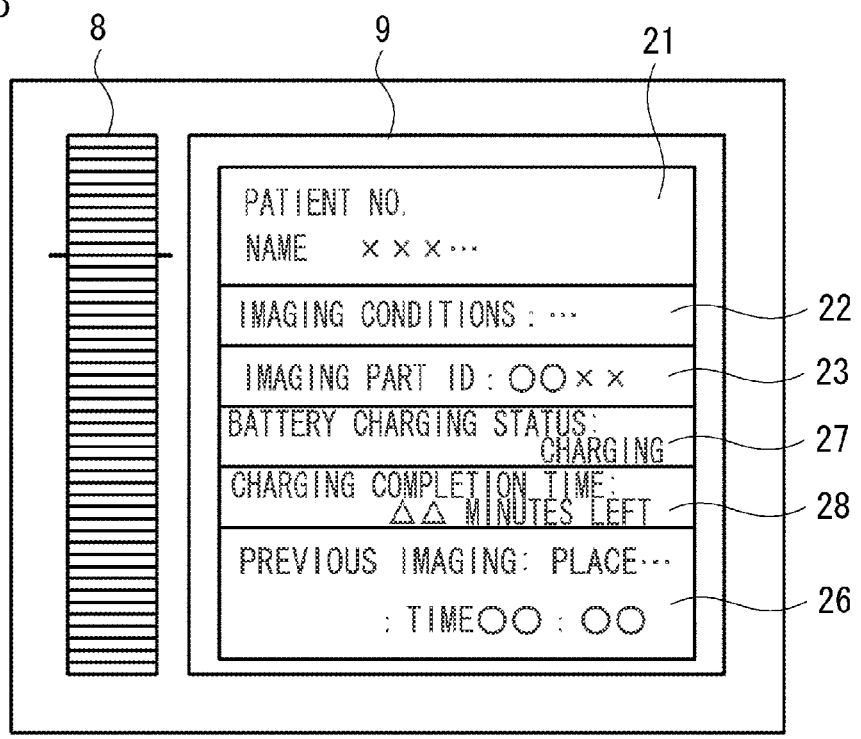

Illustrated in FIG. 3A are a screen of the signal reception state display unit 8 and a screen of the imaging information display unit 9 during the wireless communication of the imaging unit 3. FIG. 3B illustrates an example of a screen of the signal reception state display unit 8 and a screen of the imaging information display unit 9 during the wired communication of the imaging unit 3.

It is possible to confirm the signal reception state between the imaging unit 3 and the signal sending and receiving unit 6 in the wireless communication by the signal reception state display unit 8, and it is possible to confirm contact failure, cable disconnection, and the like between the cable 12 and the imaging unit 3 or the signal sending and receiving device 6 in the wired communication by the signal reception state display unit 8.

In the wireless communication illustrated in FIG. 3A, patient information 21, imaging conditions 22, an imaging part ID 23, a battery level 24 of the imaging unit 3, a battery driving time 25, an imaging history 26 are displayed on the imaging information display unit 9.

In the wired communication illustrated in FIG. 3B, the battery level 24 and the battery driving time 25 illustrated in FIG. 3A are changed to a battery charging state 27 and a battery charging completion time 28. The battery charging state 27 is the item for displaying whether charging of the battery state is in progress or charging is completed, and the battery charging completion time 28 is the item for displaying a time that is required for completion of charging. Since the electric power is supplied from the external power source 7 during the wired communication, it is unnecessary to indicate the battery level 24 and the remaining driving time 25.

By varying the display items of the wireless communication from those of the wired communication on the imaging information display unit 9 as described above, it is possible to prevent failure in distinguishing between necessary information and unnecessary information as the imaging information, and to effectively use a display region.

Figure 4:
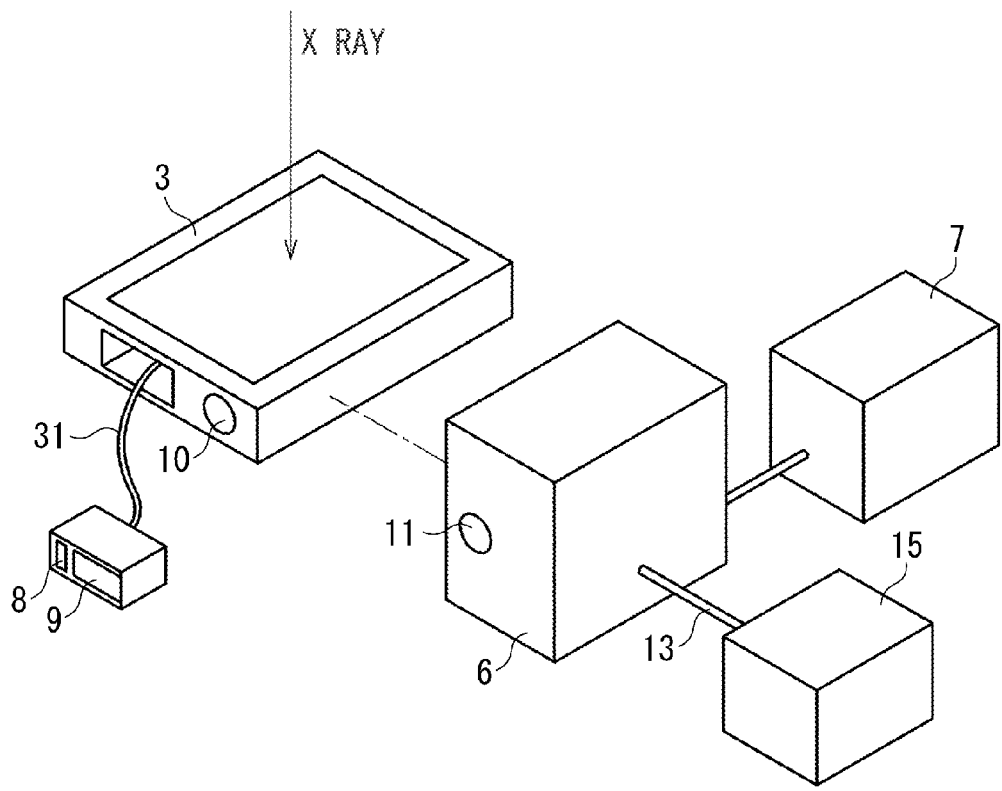
FIG. 4 is a diagram illustrating an imaging unit, a signal sending and receiving device, and an operation unit according to a second exemplary embodiment.

FIG. 4 is a diagram illustrating a second exemplary embodiment, wherein the signal reception state display unit 8 and the imaging information display unit 9 are connected to the imaging unit 3 via a cable 31. The component parts that are the same as those of the first exemplary embodiment are designated by the same reference characters. This embodiment allows the signal reception state display unit 8 and the imaging information display unit 9 to be separated from the imaging unit 3 for convenience of the operation. In other words, as illustrated, the signal reception state display unit 8 and the imaging information display unit 9 along with the cable 31 can be disposed within the body of imaging unit 3 and be removed therefrom only when necessary.

For example, in the case of using the imaging unit 3 which is inserted between the patient S and a bed or using the imaging unit 3 which is housed in the mount 2, it is sometimes difficult for the operator to confirm the signal reception state display unit 8 provided on the imaging unit 3. Therefore, the signal reception state display unit 8 and the imaging information display unit 9 are separated from the imaging unit 3 in the second exemplary embodiment, thereby making it possible to confirm the signal reception state display unit 8 and the imaging information display unit 9 in hand. Contents of the signal reception state display unit 8 and the imaging information display unit 9 are the same as those of the first exemplary embodiment.

Figure 5:
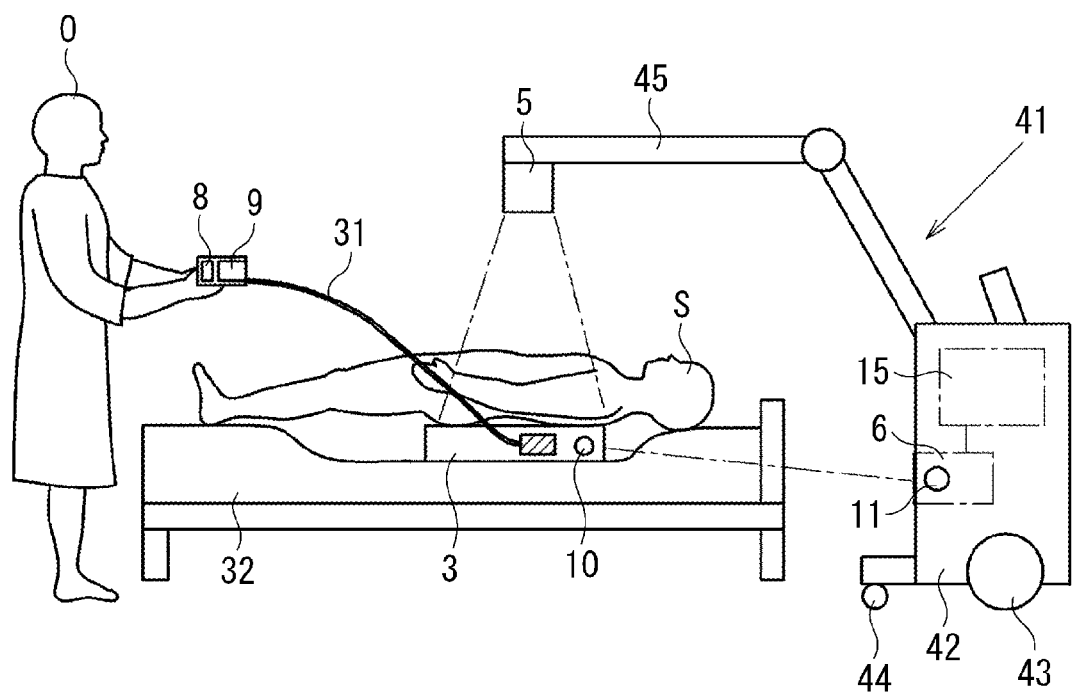
FIG. 5 is a schematic diagram illustrating a round visit imaging system according to the second exemplary embodiment.

FIG. 5 is a schematic diagram illustrating a round visit imaging system according to the second exemplary embodiment. In this illustration, an operator O performs X-ray imaging by inserting the imaging unit 3 between the bed 32 and the patient S and irradiating with an X-ray from a portable X-ray imaging device 41. In general, wheels 43 and 44 are provided at a bottom part of a main boy 42 of the portable X-ray imaging device 41 to realize movement to an arbitrary position, and the signal sending and receiving device 6 and the operation unit 15 are provided on the main body 42. Further, an arm unit 45 of which a position can be arbitrarily adjusted is attached to the main body 42, and the X-ray tube 5 is fixed to a tip of the arm unit 45.

The operation unit 15 is incorporated into the main body 42, and it is possible to operate a console (not illustrated) on an upper part of the portable X-ray imaging device 41 to perform an imaging operation. In the same manner as in the first exemplary embodiment, it is possible to apply either one of the wired communication and the wireless communication to the connection between the imaging unit 3 and the signal sending and receiving device 6 depending on the signal reception state. In this arrangement, however, the operator O can determine a signal reception state of the communication between the imaging unit 3 and the signal sending and receiving device 6 by using the signal reception state display unit 8 and the imaging information display unit 9 separated from the imaging unit 3.

Figure 6:
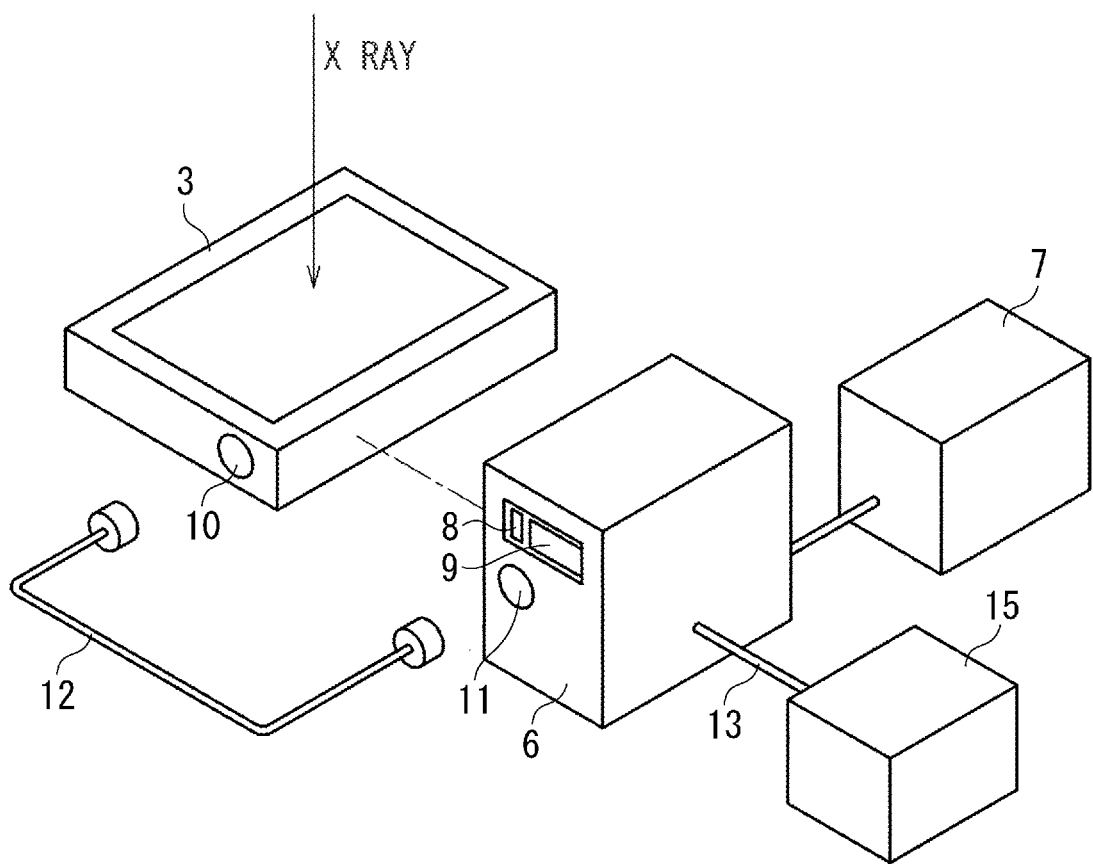
FIG. 6 is a diagram illustrating an imaging unit, a signal sending and receiving device, and an operation unit according to a third exemplary embodiment.
Figure 7:
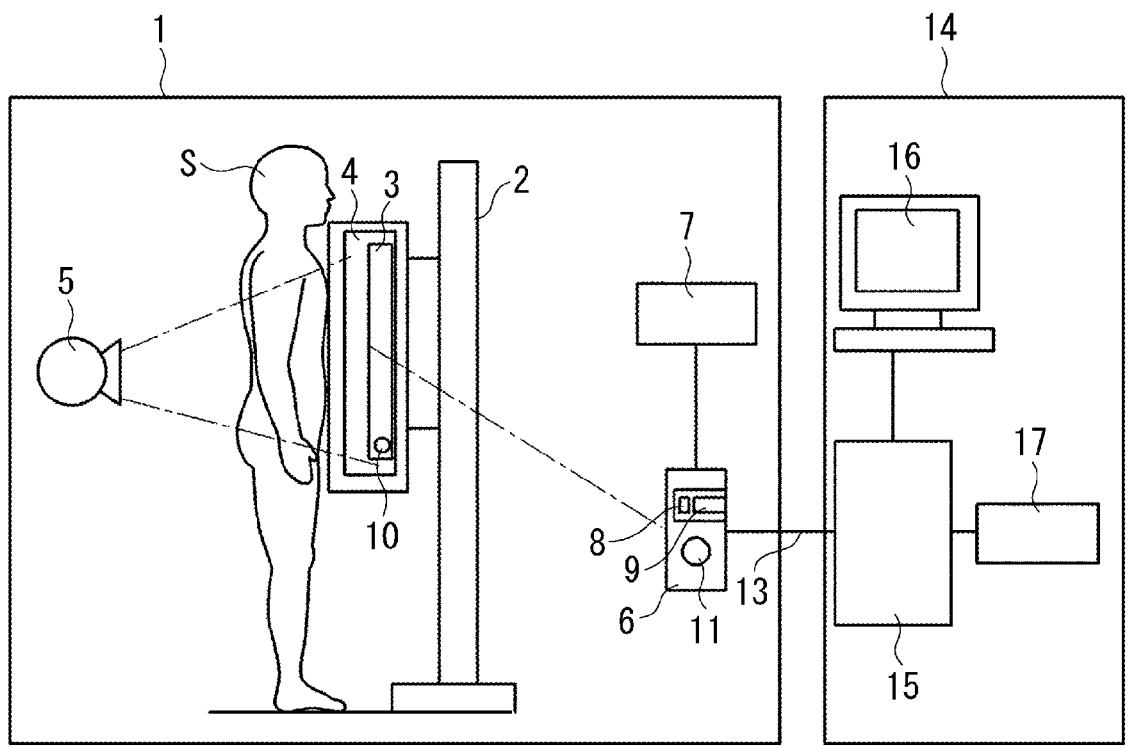
FIG. 7 is a diagram illustrating a radiographic imaging system according to the third exemplary embodiment.

FIG. 6 is a diagram illustrating a third exemplary embodiment, and FIG. 7 is a schematic diagram illustrating a radiographic imaging system intended for imaging in a hospital. The signal sending and receiving device 6 is provided with the signal reception state display unit 8 and the imaging information display unit 9. As described above, the imaging unit 3 is sometimes inserted between the patient S and the bed or housed in the mount 2. In such cases, when the signal reception state display unit 8 and the imaging information display unit 9 are provided on the imaging unit 3 as in the first and second exemplary embodiments, it is sometimes difficult for the operator to confirm the signal reception state and patient information.

Therefore, the signal reception state display unit 8 and the imaging information display unit 9 may be provided on the signal sending and receiving device 6 in the third exemplary embodiment, thereby making it possible for the operator to confirm the signal reception state display unit 8 and the imaging information display unit 9 without being influenced by an imaging state and a location of the imaging unit 3.

Also, since the signal sending and receiving device 6 and the operation unit 15 are connected to each other via the cable 13, it is possible to realize display on the imaging information display unit 9 without being influenced by the signal reception state.

The operator confirms the signal reception state from the signal reception state display unit 8 of the signal sending and receiving device 6 installed in the imaging room 1 and starts the imaging preparation when the signal reception state is appropriate for the X-ray imaging operation. However, when the signal reception state is inappropriate, the operator establishes the wired communication by connecting the cable connector 10 of the imaging unit 3 to the cable connector 11 of the signal sending and receiving device 6 via the cable 12, and, after establishing the appropriate signal reception state, starts the imaging preparation.

As described above, by providing the signal sending and receiving device 6 with the signal reception state display unit 8, the operator can confirm the signal reception state and can select a communication method appropriate for the signal reception state in the imaging room 1, thereby making it possible to diminish a resetting work for the imaging preparation.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-275498 filed Dec. 3, 2009, which is hereby incorporated by reference herein in its entirety.

What is claimed is:

1. An x-ray detector, comprising:
a battery configured to supply electric power to the x-ray detector;
a communication unit configured to communicate with an external apparatus by a communication method selected from wireless communication and wired communication;
a connector for the wired communication and for reception of electric power supply to the battery;
a display unit; and
a display control unit configured to cause the display unit to give notice of information indicating a remaining operating time of the x-ray detector in a case where the communication method between the communication unit and the external apparatus is wireless communication, and configured to not give notice of the information by using the display unit in a case where the communication method is wired communication.

2. The x-ray detector of claim 1, wherein the display control unit is configured to cause the display unit to give notice of another information indicating a charging state of the battery in a case where the communication method is wired communication.

3. The x-ray detector of claim 1, wherein the display unit comprises a first display for giving notice of the information according to the communication method, and a second display for displaying information corresponding to at least one of a communication state, a subject ID, a subject name, imaging conditions, an imaging part ID, an imaging place, and an imaging time, and
wherein the display control unit is configured to cause the display unit to give notice, by using the first display, of the information indicating the remaining operating time of the x-ray detector in a case where the communication method is wireless communication, and configured to not give notice of the information indicating the remaining operating time by using the first display in a case where the communication method is wired communication.

4. The x-ray detector of claim 1, wherein the display unit is provided on a surface except for an x-ray incident surface of the x-ray detector.

5. The x-ray detector of claim 1, wherein the connector is configured to be connected to a cable for the wired communication.

6. The x-ray detector of claim 1, wherein the battery is configured to be charged by electric power supplied through the connector.

7. The x-ray detector of claim 1, wherein the display control unit is configured to cause the display unit to give notice of another information different from the information indicating the remaining operating time of the x-ray detector, in a case where the communication method is wired communication.

8. The x-ray detector of claim 1, wherein
the display unit includes a first display and a second display,
the display control unit is configured to cause the first display to give notice of the information in a case where the communication method is wireless communication and to cause the first display to give notice of information different from the information indicating the remaining operating time in a case where the communication method is wireless communication, and
the display control unit is configured to cause the second display to display information different from the information indicating the remaining operating time in a case where the communication method is wired communication and wireless communication.

9. A control unit for displaying information about an x-ray sensor on a display unit, comprising:
a communication unit configured to connect the x-ray sensor to an external apparatus by a communication method selected from wired communication and wireless communication; and
a display control unit configured to control a display unit to give notice of information indicating a remaining operating time of the x-ray sensor by using a specific display region of the display unit in a case where the communication method is wireless communication, and configured to not give notice of the information by using the specific display region in a case where the communication method is wired communication.

10. An x-ray imaging system, comprising:
an x-ray detector comprising a battery;
an operation unit configured to control the x-ray detector;
a signal sending and receiving device configured to mediate communication between the x-ray detector and the operation unit by a communication method selected from wired communication and wireless communication; and
a display unit configured to give notice of information indicating a remaining operating time of the x-ray detector using a specific display region of the display unit in a case where the x-ray detector performs communication through the signal sending and receiving device by wireless communication, and configured to not give notice of the information by using the specific display region of the display unit in a case where the x-ray detector performs communication through the signal sending and receiving device by wired communication.

11. The x-ray imaging system of claim 10, wherein a type of information given by the specific display region is changed depending on the communication method between the x-ray detector and the signal sending and receiving device.

12. The x-ray imaging system of claim 10, further comprising a cable connecter, provided on a surface except for an x-ray incident surface of the x-ray detector, for connecting cables for the wired communication between the x-ray detector and the signal sending and receiving device.

13. The x-ray imaging system of claim 10, wherein the x-ray detector comprises a warning unit which is separate from the display unit, and the warning unit emits a warning when a signal reception state of the wireless communication is not appropriate for x-ray imaging.

14. A control method for controlling a display unit to display a state of an x-ray detector, the x-ray detector including a battery for supplying electric power to the x-ray detector and a communication unit for communicating with an external apparatus by one of wired communication and wireless communication, the control method comprising:
acquiring information indicating communication between the x-ray detector and the external apparatus; and
causing the display unit to give notice of information indicating a remaining operating time of the x-ray detector on the display unit in a case where the communication between the x-ray detector and the external apparatus is by wireless communication, and to not give notice of the information in a case where the communication is wired communication.

15. An x-ray detector, comprising:
a battery configured to supply electric power to the x-ray detector;
a communication unit configured to communicate with an external apparatus by a communication method selected from wireless communication and wired communication;
a connector for the wired communication and for reception of electric power supply to the battery;
a display unit; and
a control unit configured to cause the display unit to give notice of information indicating a remaining operating time of the x-ray detector in a case where the communication method between the communication unit and the external apparatus is wireless communication, and configured to inhibit the display unit from giving notice of the information in a case where the communication method is wired communication.

16. A control unit for displaying information about an x-ray sensor on a display unit, comprising:
- a communication unit configured to connect the x-ray sensor to an external apparatus by a communication method selected from wired communication and wireless communication; and
- a control unit configured to give notice of information indicating a remaining operating time of the x-ray sensor by using a specific display region of a display unit in a case where the communication method is wireless communication, and configured to inhibit the display unit from giving notice of the information by using the specific display region in a case where the communication method is wired communication.

17. An x-ray imaging system, comprising
- an x-ray detector comprising a battery;
- an operation unit configured to control the x-ray detector;
- a signal sending and receiving device configured to mediate communication between the x-ray detector and the operation unit by a communication method selected from wired communication and wireless communication; and
- a control unit configured to give notice of information indicating a remaining operating time of the x-ray detector by using a specific display region of a display unit in a case where the x-ray detector performs communication through the signal sending and receiving device by wireless communication, and configured to inhibit the display unit from giving notice of the information by using the specific display region in a case where the x-ray detector performs communication through the signal sending and receiving device by wired communication.

18. A control method for controlling a display unit to display a state of an x-ray detector, the x-ray detector including a battery for supplying electric power to the x-ray detector and a communication unit for communicating with an external apparatus by one of wired communication and wireless communication, the control method comprising:
- acquiring information indicating communication between the x-ray detector and the external apparatus;
- causing the display unit to give notice of information indicating a remaining operating time of the x-ray detector on the display unit in a case where the communication between the x-ray detector and the external apparatus is by wireless communication; and
- inhibiting the display unit from giving notice of the information in a case where the communication between the x-ray detector and the external apparatus is by wired communication.

19. An x-ray detector, comprising:
- a battery configured to supply electric power to the x-ray detector;
- a communication unit configured to communicate with an external apparatus by a communication method selected from wireless communication and wired communication;
- a connector for the wired communication and for reception of electric power supply to the battery;
- a display unit; and
- a display control unit configured to cause the display unit to give notice of information indicating a remaining operating time of the x-ray detector in a case where the communication method between the communication unit and the external apparatus is wireless communication, and not to give notice of the information by using the display unit in a case where the communication method is wired communication.

\* \* \* \* \*